United States Patent [19]

Gilbert et al.

[11] Patent Number: 5,211,870
[45] Date of Patent: May 18, 1993

[54] MALODOR-FREE CLEANSING BAR COMPOSITION CONTAINING ZEOLITE ODOR CONTROLLING AGENT

[75] Inventors: Lawrence A. Gilbert, West Chester; Danielle L. Fieldstad, Cincinnati; Sherri V. Cox, West Chester; Diane L. Furio, Cincinnati; Wayne E. Eccard, Cleves; Neil W. Jordan, Cincinnati, all of Ohio

[73] Assignee: The Procter & Gamble Company, Cincinnati, Ohio

[21] Appl. No.: 850,173

[22] Filed: Mar. 11, 1992

[51] Int. Cl.$^5$ ............ A61K 7/50; C11D 3/12; C11D 9/20; C11D 17/00
[52] U.S. Cl. .................... 252/120; 252/117; 252/121; 252/123; 252/128; 252/129; 252/130; 252/131; 252/134; 252/174; 252/174.23; 252/174.24; 252/174.25; 252/DIG. 5; 252/DIG. 16; 424/76.1; 424/76.9; 424/464; 424/684; 514/970
[58] Field of Search ........... 252/121, 123, 128, 129, 252/130, 131, 120, 134, 174, DIG. 16, 174.25; 502/62, 78, 411; 424/69, 76.1, 76.9, 464, 684

[56] References Cited

U.S. PATENT DOCUMENTS

| | | | |
|---|---|---|---|
| 2,714,093 | 7/1955 | Blumenthal | 252/113 |
| 2,734,870 | 2/1956 | Lewis | 252/558 |
| 4,335,025 | 6/1982 | Barker | 252/550 |
| 4,362,715 | 12/1982 | Strianse et al. | 424/78 |
| 4,437,429 | 3/1984 | Goldstein et al. | 119/1 |
| 4,539,131 | 9/1985 | Garner-Gray | 252/99 |
| 4,666,624 | 5/1987 | Irlam et al. | 252/134 |
| 4,692,261 | 9/1987 | Filomeno | 252/105 |
| 4,719,030 | 1/1988 | Williams et al. | 252/133 |
| 4,769,173 | 9/1988 | Cornelissen et al. | 252/174.12 |
| 4,795,482 | 1/1989 | Gioffre et al. | 55/75 |
| 4,822,349 | 4/1989 | Hursey et al. | 604/367 |
| 4,826,497 | 5/1989 | Marcus et al. | 604/359 |
| 4,855,154 | 8/1989 | Gioffre et al. | 426/417 |
| 4,961,881 | 10/1990 | Ou | 260/428.5 |
| 5,013,486 | 5/1991 | Joshi | 252/559 |
| 5,039,453 | 8/1991 | Joshi et al. | 252/540 |
| 5,041,243 | 8/1991 | Joshi | 252/534 |
| 5,053,159 | 10/1991 | Joshi | 252/106 |
| 5,084,427 | 1/1992 | Tsoucalas | 502/62 |
| 5,096,608 | 3/1992 | Small | 252/132 |

FOREIGN PATENT DOCUMENTS

| | | |
|---|---|---|
| 898279 | 10/1989 | South Africa . |
| 2060676A | 5/1981 | United Kingdom . |
| 2096163A | 10/1982 | United Kingdom . |
| 2099013A | 12/1982 | United Kingdom . |
| 2189255A | 10/1987 | United Kingdom . |
| 2238316A | 5/1991 | United Kingdom . |

Primary Examiner—Dennis Albrecht
Attorney, Agent, or Firm—Leonard Williamson

[57] ABSTRACT

A malodor-free personal cleansing bar with a low level of zeolite odor-controlling agent. The preferred application is a fragrance-free bar, a scented bar, or the like.

12 Claims, No Drawings

MALODOR-FREE CLEANSING BAR COMPOSITION CONTAINING ZEOLITE ODOR CONTROLLING AGENT

TECHNICAL FIELD

The present invention relates to personal cleansing bars with an odor-controlling agent which is especially useful in odorless and/or bars for increasing fragrance quality in scented bars The odor-controlling agents herein are designed to combat a broad spectrum of odoriferous materials, including, but not limited to, fatty acid, amine, ketone, and aldehyde-type odors.

BACKGROUND OF THE INVENTION

A wide variety of clays and zeolites designed as fillers and for bar properties are known in the literature.

One particular aspect of personal cleansing bars is to deliver a product with acceptable odor. Many materials used in cleansing bars have an unpleasant odor, or develop such odors when in contact with air and/or bacteria for prolonged periods. The literature is replete with references relating to odor control in products such as soap bars, detergents, diapers and catamenials.

Various odor-controlling agents have been disclosed in the literature. In particular, certain zeolitic materials are becoming known for their odor-controlling properties. Zeolitic materials, per se, have been used in soap bars; e.g., U.S. Pat. No. 4,719,030, Williams et al., issued Jan. 12, 1988, for a translucent soap bar containing sodium aluminosilcate. Zeolites have been also used in laundry bars.

However, the use of odor controlling zeolite in personal cleaning bars and in particular malodor free and/or odorless mild synthetic detergent cleansing bars is believed to be novel.

The patent literature contains a considerable number of references relating to zeolites, per se, and to cleansing bars, per se.

Various other patents relating to various personal cleansing bar materials and to zeolites are listed in the Detailed Description and Examples, hereinafter. All documents cited in this specification are incorporated herein by reference

SUMMARY OF THE INVENTION

The present invention encompasses a personal cleansing bar which is essential free of raw material base malodor comprising a cohesive mixture of a cleansing bar base material selected from the group consisting of soaps, free fatty acids, waxes, cationic polymers, synthetic surfactants and mixtures, a water-insoluble odor-controlling agent, and water.

The present invention also encompasses: a personal cleansing liquid essentially free of raw material malodors comprising a cohesive mixture of an odoriferous cleansing liquid raw material selected from the group consisting of soaps, free fatty acids, waxes, cationic polymers, synthetic surfactants and mixtures, a water-insoluble odor-controlling agent, and water.

The invention is particularly applicable to synthetic-based bars where greater than 50% of the surfactant is synthetic surfactant. In particular, it relates to dramatically reducing the base formula malodors in order to produce fragrance-free bars with acceptable scent profiles, and fragrance bars with improved scent profiles.

The term base formula refers to the composition of the bar without perfume or zeolite.

The odor-controlling agent typically comprises greater than 0.1% by weight of the final composition. (For purposes of clarity, the percentage loading of the odor-controlling agent, e.g., zeolite, is calculated on the total weight of the final particles.)

The cleansing bar raw materials base herein are selected from the group consisting of alkyl sulfate, acyl isethionate, alkyl sarcosinate, alkyl glyceryl ether sulfonate, paraffin wax, sodium acyl sarcosinate, stearic acid, lauric acid coconut acid, soap, sodium isethionate, sodium chloride, water, cationic polymer, and mixtures thereof.

Preferred particulate odor-controlling (odor-reducing) agents used herein comprise a member selected from the group consisting of intermediate $(SiO_2/Al_2O_3)Y$ zeolites, mordenites, large pore beta zeolites, and mixtures thereof.

A preferred zeolite is substantially free of particles sized greater than 30 microns, and in fact is substantially free of particles sized over 15 microns for acceptable bar fee. "Substantially free" means that the larger particles are less than about 5%, preferably less than about 4%, more preferably less than about 3%, as measured by laser light scattering.

The composition comprises a personal cleansing bar formula and at least 0.05% to 5% (preferably at least 0.2%) by weight of a particulate odor-controlling agent selected from zeolite. The level, of course, depends upon the level and type of malodor present in the particular base formula one is working with and should be adjusted accordingly.

For application to fragrance-free bars, enough zeolite is added to the base formula to reduce the amount of odor present in the bar to a desirable level. In a normal milled bar soap process, the zeolite may be added to the mix/reaction tank at the beginning of the process, or to the amalgamator. Higher levels of zeolite may be used in order to adsorb any odors that may evolve in the formula over time.

For application to scented bars, sufficient zeolite is added to the base formula at the mix/reaction tank to cover any malodors present. At this point the zeolite should be saturated or near saturation with volatile components. Further down the process, at the amalgamator, perfume is added and the formula is processed as it normally would be. Because of the saturated or near saturated state of the zeolite at this point, if any perfume is adsorbed at all, it should only be some of the perfume topnotes. Because the fragrance is no longer competing with the base formula malodor, the resulting bar will have an overall higher quality fragrance. Care should be exercised to add only an effective amount of the zeolite so as not to adsorb too much of the perfume.

All percentages, ranges and ratios herein are by weight, unless otherwise specified.

DETAILED DESCRIPTION OF THE INVENTION

The compositions and methods for controlling odors in the manner of this invention involve the use of zeolitic-type materials as described more fully hereinafter.

The bars which employ said zeolitic odor-control technology disclosed herein can be prepared using constituents that are otherwise very well-known in current commercial practice, and reference can be made to the various patents mentioned herein and to the general personal cleansing products patent literature and trade catalogues for such items. Likewise, methods and apparatus for making personal cleansing bars and the like are known from patents and engineering literature.

While the constituents used in personal cleansing bars, and the like, are well-known, the following may be mentioned by way of example.

It is to be understood that the present invention also includes the use of malodor-controlling zeolite in liquid cleansing compositions.

The bars and liquid cleansers which employ said zeolitic odor-control technology disclosed herein can be prepared using constituents that are otherwise very well-known in current commercial practice, and reference can be made to the various patents mentioned herein and to the general personal cleansing products patent literature and trade catalogues for such items. Such bars and liquids typically comprise an odoriferous base material selected from the group consisting of soaps, fatty acids, waxes, silk proteins, synthetic surfactants, and the like. Likewise, methods and apparatus for processing personal cleansing bars and liquids, and the like, are known from patents and engineering literature.

It is to be understood that the present invention resides in the novel use of odor-controlling adsorbent materials in the personal cleansing bars and liquids disclosed herein, rather than in the constituents per se.

Zeolite Odor-Controlling/Odor-Reducing Agent

The manufacture of zeolite materials of the type used in the practice of this invention is well-known, and reference can be made to the voluminous literature for typical synthetic procedures.

In order to assist the formulator and user of the compositions, articles and methods of this invention (but not by way of limitation), attention is directed to the synthetic procedures described in the following reference texts: ZEOLITE SYNTHESIS, ACS Symposium Series 398, Eds. M. L. Occalli and H. E. Robson (1989) pages 2–7; ZEOLITE MOLECULAR SIEVES, Structure, Chemistry and Use, by D. W. Breck, John Wiley & Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University Microfilms International, Ann Arbor, Mich., pages 2–8.

It is to be understood that the preferred zeolites used herein are not of the fibrous type, e.g., various mordenites and some type Y zeolites, since these may cause asbestos-type safety issues. Accordingly, the term "zeolite" as used herein is intended to encompass only the non-fibrous zeolites. Moreover, it is preferred that the zeolites used herein be substantially hydrophobic, since they generally must function to adsorb odors in the presence of water when used in the compositions and processes disclosed herein. While some naturally-occurring zeolites meet the objectives of this invention, the synthetic zeolites of the types available in commerce are generally more preferred.

In general terms, traditional zeolites comprise an aluminate/silicate framework, with associated cations, M, providing overall electrical neutrality. Empirically, the zeolite framework can be represented as $$x\,AlO_2 \cdot y\,SiO_2$$

and the electrical neutral zeolite as $$x/n\,M \cdot x\,AlO_2 \cdot y\,SiO_2 \cdot z\,H_2O$$

wherein: x and y are each integers, M is a cation and n is the charge on the cation. As noted by the empirical formula, zeolites may also comprise waters of hydration (z $H_2O$). Reference to the literature will illustrate that M can be a wide variety of cations, e.g., $Na^+$, $K^+$, $NH_4^+$, alkylammonium, heavy metals and the like. The practice of the present invention does not require any particular selection of cation; accordingly, sodium ion is convenient and preferred.

It is to be understood that a first class of preferred zeolites used herein has entirely different ratios of $(SiO_2/Al_2O_3)Y$ than the zeolites disclosed in U.S. Pat. Nos. 4,795,482 and 4,826,497. Stated otherwise, the ratio of integers x and y in this first class of zeolites is such that the zeolites are typically characterized as intermediate" silicate/aluminate zeolites, whereas those of U.S. Pat. Nos. 4,795,482 and 4,826,497 are "high" silicate/aluminate zeolites.

While not intending to be limited by theory, it appears that the silicate/aluminate ratios of the "intermediate" zeolites used in the practice of this invention result in several advantages over the "high" zeolites. First, the intermediate zeolites have a higher capacity for amine-type odors, e.g., those associated with some polymers, than the high zeolites. This is important to controlling odors. Second, the intermediate zeolites have a larger surface area (700–800 than the high zeolites (ca. 400 m²/g). This results in more efficient odor adsorptivity, on a wt./wt. basis; or, in the alternative, allows less zeolite to be used to adsorb a given amount of odor. Third, the intermediate zeolites appear to be somewhat more tolerant to moisture, and retain more of their odor-adsorbing capacity in the presence of water.

Preferred Zeolite Molar Ratio

The intermediate zeolites used in this invention are characterized by $(SiO_2/Al_2O_3)Y$ molar ratios of less than about 10. Typically, the molar ratio of $(SiO_2/Al_2O_3)Y$ will range from about 2 to about 10, preferably about 3 to about 8.

The synthesis of intermediate zeolites forms no part of the present invention since various syntheses are known in the extensive zeolite literature. The following is given simply by way of illustration, and not limitation, of a synthetic procedure.

While different starting materials can yield different zeolites, the same zeolite can be made from different reactants. Some reactant variables influencing the structure and composition of the final zeolite are:

the identity, ratio and order of addition of the reactants;
the strength of the base;
the temperature (ambient to ca. 100° C.);
mechanical agitation such as stirring; and
the gelation time (1 hour to days).

Once the desired gelation is achieved, the gel is transferred to a Teflon or stainless steel container and placed in an autoclave. Crystal formation begins as the gel is subjected to constant or variable temperature at autogeneous pressure for an indefinite time. There are basically three recognized phases during transformation of the gel to crystals. The phases are: (1) induction or nucleation (first crystal appears); (2) crystal growth; and (3) phase transformation. Some factors influencing the rate at which crystals form and grow are the temperature, pH, addition of seed crystals or templating materials for structure directing, stirring and centrifugation.

After phase transformation, the slurry is removed from the autoclave and filtered. The crystals are washed and dried at ca. 100° C. Further modifications are possible if so desired.

Post-Synthesis Modifications

Some post-synthesis modifications are a means of obtaining other traditional zeolites. For instance, counter ions can be exchanged such as:

Na—zeolite+NH$_4$Cl→NH$_4$—zeolite or

Na—zeolite+HCl→H—zeolite imparting unique adsorptive forces and modifying the pore size of, for example, an A, X or Y zeolite. Additionally, stabilization of traditional zeolites is possible. For example, a typical method of synthesizing an ultrastable zeolite Y (USY) such as "VALFOR CP300-56" is as follows:

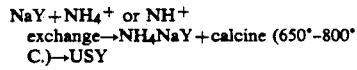

NaY+NH$_4^+$ or NH$^+$
exchange→NH$_4$NaY+calcine (650°–800° C.)→USY

Synthesis of Stabilized Zeolites

Several post-synthesis modification methods exist for making special zeolites. The methods include (1) pore modification; (2) surface modification; and (3) structural change. The first two methods consist of adsorbing species by chemical vapor deposition inside or on the zeolite. Pore modifiers such as SiH$_4$ and BH$_3$ and surface modifiers such as Si(OCH$_4$)$_4$, SiCl$_4$, TiCl$_4$ and SeCl$_4$ have been used to impart new unique properties to the zeolite. The most frequently used structural change method is to remove alumina from the main framework (i.e., de-aluminate). De-alumination can be performed by one of several routes such as (1) acid leaching; (2) steam (700°–900° C.); or (3) treatment with SiCl$_4$ at cold temperatures. An example of de-alumination is:

Zeolite Y+H$_4$EDTA de-aluminated Zeolite Y

The following references further illustrate the synthesis of intermediate zeolites of the type employed herein: Lok, B. M., Cannan, T. R., and Messina, C. A., "The Role of Organic Molecules in Molecular Sieve Synthesis" Zeolites 3, 282–291 (1983); Barrer, R. M. "Zeolites and Their Synthesis" Zeolites 1, 130–140 (1981); ZEOLITES FOR THE NINETIES, Proceedings of the 8th International Zeolite Conference, Eds. P. A. Jacobs and R. A. van Santen (1989) pages 119–372; and MOLECULAR SIEVES, Adv. Chem. Ser. 121, Eds. W. M. Meier and J. B. Uytterhoeven (1973).

A wide variety of intermediate zeolites suitable for use herein are commercially available from commercial suppliers such as PQ Corporation; Mobil; and UOP. Such materials are sold under various commercial and trade names such as VALFOR CP 301-68, VALFOR 300-63, VALFOR CP300-35 and VALFOR 300-56, and the CBV100 series (other than mordenite, as noted above) of zeolites from Conteka.

A second type of odor-controlling agent which can be employed in the practice of this invention for odor adsorption comprises the "high ratio" zeolites. Such materials include, for example, the well-known "molecular sieve" zeolites of the ZSM, beta zeolite, etc., type (generally in the 1–10 micron particle size range) and the zeolite materials marketed under the trade name ABSCENTS by the Union Carbide Corporation and UOP, and which are typically available as a white powder in the 3–5 micron particle size range (see: ABSCENTS, A New Approach for Odor Control, by A. J. Gioffre, copyright 1988 by the Union Carbide Corporation). The particle size range for ABSCENTS is too large for the preferred bars of this invention. However, such materials are preferred over the "intermediate" zeolites when control of odors associated with sulfur compounds, e.g., thiols, mercaptans, as well as some control of amine odors, is desired.

The use of zeolites of the ABSCENTS type to control odors is fully described in U.S. Pat. No. 4,795,482, issued Jan. 3, 1989, to Gioffre and Marcus. In general, these molecular sieve odor-controlling agents appear to function by entrapping by chemical adsorption odoriferous substances within their molecular lattice structures. Whatever their mode of action, these odor-controlling agents can be characterized by their physical parameters, as follows. These agents are reported by Gioffre and Marcus to be crystalline siliceous molecular sieves in which at least about 90%, and preferably at least about 95%, of the framework tetrahedral oxide units are SiO$_2$ tetrahedra and which have a sorptive capacity for water at 25° C. and 4.6 of less than 10 weight percent. In the case of aluminosilicate molecular sieves, those "high ratio" zeolite odor-controlling agents have a framework (SiO$_2$/Al$_2$O$_3$)Y molar ratio of from about 35 to infinity, and preferably from 200 to 500. Such siliceous molecular sieves have a pore diameter of at least 5.5 Angstroms, preferably at least 6.2 Angstroms. Preferably the adsorption capacity for water vapor at 25° C. and a water vapor pressure (p/p$_0$) of 4.6 is less than 6 weight percent. As stated by Gioffre and Marcus, the efficacy of these molecular sieves is not dependent on the presence of the water of hydration in the internal cavitius of the microporous structure as a result of their hydrothermal formation. In fact, at least a major proportion, usually substantially all, of this original water of hydration is removed in the process of removing any pore-blocking templating agent which may be present in the adsorbent. Calcination effectively removes any organic moieties. Also, water washing, leaching or washing with a caustic or dilute mineral acid solution is advantageously utilized to remove extraneous synthesis reactants from the pore system. Lowering of the alkali metal content, particularly the non-zeolitic, i.e., occluded alkali metal compounds can also be beneficial. These procedures also serve to remove the original water of hydration.

As further disclosed by Gioffre and Marcus, such siliceous molecular sieves include the microporous crystalline aluminosilicates, i.e., the zeolitic molecular sieves as well as the so-called silica polymorphs. With respect to the latter compositions, their crystal lattices are ideally formed entirely of SiO$_2$ tetrahedral units, but the as-synthesized forms commonly contain at least trace amounts of aluminum derived from aluminum impurities in the synthesis reagents. The aluminosilicate molecular sieves comprise the large class of well-known crystalline zeolites. These high-silica molecular sieves are either commercially available or are prepared by methods well-known in the art, involving direct hydrothermal synthesis or involving certain types of crystal lattice dealuminations. A comprehensive review article by E. M. Flanigen concerning both "high Si/Al zeolites and silica molecular sieves is published in Proc. 5th Int. Conf. Zeolites, Naples, 1980", L. V. C. Rees, ed., Heyden, London, pp. 760–780. It is to be understood that all such materials are referred to herein simply as "zeolites", for convenience.

With respect to the foregoing ABSCENTS odor-controlling agents, it is important that their pore system be open so that the internal cavities of the crystals be accessible to the odor molecules. In the case of the aluminosilicates or silica polymorphs produced using large organic templating ions such as tetraalkylammonium ions, it is necessary to remove charge balancing organic ions and any occluded templating material in order to permit adsorption of the odor molecules. In such a removal process and also in the removal of inorganic debris, the original water of hydration is also removed. Upon exposure to the atmosphere, a portion of the water of hydration is reacquired, but this does not affect the characteristics of the molecular sieves which are preferred for the practice of the present invention, i.e., the molecular sieves can be employed in either a hydrated or dehydrated state, but, in general, the dehydratad state is preferred. In the case of most of the dealumination procedures referred to above, the original water of dehydration is also removed, and can similarly be replaced, if desired, for the practice of the invention.

More specifically, Gioffre and Marcus disclose that the class of their disclosed medium to large pore siliceous molecular sieves, from which the original, as-synthesized water of hydration has been substantially removed, and which have a capacity for adsorbed water of not greater than 10, and preferably not greater than 6, weight percent when measured at 25° C. and a water vapor pressure ($p/p_0$) of 4.6, function in an extraordinary manner with respect to odor elimination. Many of the synthetic zeolites prepared using organic templating agents are readily prepared in a highly siliceous form—some even from reaction mixtures which have no intentionally added aluminum. These zeolites are markedly organophilic and include ZSM-5 (U.S. Pat. No. 3,702,886); ZSM-11 (U.S. Pat. No. 3,709,979); ZSM-35 (U.S. Pat. No. 4,016,245); ZSM-23 (U.S. Pat. No. 4,076,842); and ZSM-38 (U.S. Pat. No. 4,046,859) to name only a few. According to these authors, the silica molecular sieves known as silicalite and F-silicalite are particularly suitable for use as odor-controlling agents. These materials are disclosed in U.S. Pat. Nos. 4,061,724 and 4,073,865, respectively. To the extent the aforesaid siliceous sieves are synthesized to have ($SiO_2/Al_2O_3$)Y ratios greater than 35, they are frequently suitable for use in the present articles without any additional treatment to increase their degree of hydrophobicity. Molecular sieves which cannot be directly synthesized to have both the desired high Si/Al and/or degree of hydrophobicity ratios can be subjected to dealumination techniques, fluorine treatments and the like, which result in organophilic zeolite products. High-temperature steaming procedures for treating zeolite Y which result in hydrophobic product forms are reported by P. K. Maher et al., "Molecular Sieve Zeolites., Advan. Chem. Ser. 101, American Chemical Society, Washington, D.C., 1971, p. 266. A more recently reported procedure applicable to the manufacture of "high" zeolite species generally, involves dealumination and the substitution of silicon into the dealuminated lattice site. This process is disclosed in U.S. Pat. No. 4,503,023 issued Mar. 5, 1985 to Skeels et al. Halogen or halide compound treatments for zeolites to increase their hydrophobicity are disclosed in U.S. Pat. Nos. 4,569,833 and 4,297,335. Steam-treated zeolite Y, prepared per U.S. Pat. No. 4,331,694, and denominated LZ-10", is a particularly useful odor-controlling agent.

Various other modified zeolite-type materials, such as the manganese-aluminum-phosphorus-silicon-oxide molecular sieves described in U.S. Pat. No. 4,793,833, Lok et al., assigned to UOP, can be used herein. See also U.S. Pat. Nos. 4,604,110; 4,437,429; and 4,648,977, for other zeolitic odor-controlling compositions.

Mixtures of zeolites, especially mixtures of the aforementioned "intermediate" and "high" ($SiO_2/Al_2O_3$)Y zeolites, can also be used in the practice of this invention, according to the desires of the formulator.

Optional Adjunct Odor-Controlling Materials

The compositions and articles of this invention can also contain an effective, i.e., odor-controlling, amount of various additional non-zeolite odor-controlling materials to further expand their capacity for controlling odors as well as the range of odor types being controlled. Such materials include, for example, cetyl pyridinium chloride, zinc chloride, EDTA, etidronate, BHT, and the like.

A preferred bar of this invention is an improved, malodor free, mild personal cleansing syndet bar comprising: a zeolite adsorbing agent, long chain $C_{15}$–$C_{22}$ alkyl or acyl synthetic surfactant having essentially saturated, preferably $C_{16}$–$C_{18}$, alkyl chains, soap, free fatty acid, a lathering mild surfactant comprising $C_{12}$–$C_{18}$ acyl (cocoyl) isethionate, a selected paraffin wax, and optionally, but preferably, a cationic polymer. More specifically, the composition comprises an effective amount of a malodor adsorbing zeolite and:

A. from about 4% to about 32% of essentially saturated long chain ($C_{15}$–$C_{22}$ alkyl) synthetic surfactant selected from the group consisting of: alkyl sulfate, acyl isethionate, alkyl sarcosinate, alkyl glyceryl ether sulfonate, and mixtures thereof;

B. from about 4% to about 30% of paraffin wax having a melting point of from about 130° F./54° C. to about 180° F./82° C.;

C. from about 20% to about 70% lathering mild synthetic surfactant; and wherein said lathering mild synthetic surfactant is selected from $C_{12}$–$C_{18}$ acyl isethionate, $C_{12}$–$C_{14}$ alkyl glyceryl ether sulfonate, $C_{12}$–$C_{14}$ acyl sarcosinate, and mixtures thereof, preferably as their sodium salts; and wherein at least about 10% of said bar is said mild lathering $C_{12}$–$C_{18}$ acyl isethionate;

D. from about 2% to about 30% free fatty acid;

E. from 0% to about 15%, preferably from about 2% to about 10%, soap;

F. from about 2% to about 8% sodium isethionate;

G. from 0% to about 2% sodium chloride;

H. from about 1.5% to about 10% water;

I. from 0% to about 5% of cationic polymer; and

J. from 0% to about 2% perfume;

wherein said bar has a pH of from about 4.0 to about 9.0.

When the level of $C_{12}$–$C_{18}$ mild surfactant is from about 40% to about 70% by weight of the bar, the ratio of said stearic acid to said lauric acid (or coconut acid) is preferably from about 5:1 to about 10:1.

When the level of $C_{12}-C_{18}$ mild surfactant is from about 30% to about 45%, the ratio of said stearic acid to said lauric acid (or coconut acid) is preferably from about 2:1 to about 6:1.

When the level of $C_{12}-C_{18}$ mild surfactant is from about 20% to about 35%, the ratio of said stearic acid to said lauric acid (or coconut acid) is preferably from about 0:1 to about 2:1.

The present invention provides such an improved syndet bar comprising: (1) from about 4% to about 32%, preferably from about 5% to about 30%, of $C_{15}-C_{22}$, preferably $C_{16}-C_{18}$, essentially saturated long chain alkyl sulfates; acyl isethionate, alkyl sarcosinate, alkyl glyceryl ether sulfonate and mixtures thereof; (2) from about 20% to about 70%, preferably from about 30% to about 60%, by weight of said bar, of mild high lathering, synthetic surfactants with at least about 10% by weight of the bar being $C_{12}-C_{18}$ acyl isethionate; (3) from about 2% to about 30%, preferably from about 3% to about 20%, cf $C_{10}-C_{22}$, preferably $C_{12}-C_{18}$, essentially saturated fatty acids; (4) from 0% to about 15%, preferably from about 2% to about 10% $C_{10}-C_{22}$, preferably $C_{12}-C_{18}$, alkali metal soaps, preferably sodium or potassium soaps; (5) from about 4% to about 30%, preferably From about 5% to about 28%, paraffin wax with an average melting point of from about 130° F. to about 180° F., preferably from about 140° F. to about 165° F., more preferably from about 142° F. to about 160° F.; (6) from 0% to about 10% auxiliary plastic binders such as polyethylene glycols and/or monoglyceride; (7) from about 1.5% to about 10%, preferably from about 2% to about 8%, more preferably from about 3% to about 6%, water; (8) from 0% to about 2% sodium chloride; (9) from about 2% to about 8% sodium isethionate; (10) From 0% to about 5%, preferably from about 0.3% to about 4% of cationic polymer; and (11) the zeolite at the preferred levels; the pH of the bar is from about 4 to about 9, preferably from about 5 to about 8.

When the level of $C_{12}-C_{18}$ mild surfactant is from about 40% to about 70% by weight of the bar, the ratio of said stearic acid to said lauric acid is from about 5:1 to about 10:1.

When the level of $C_{12}-C_{18}$ mild surfactant is from about 30% to about 45%, the ratio of said stearic acid to said lauric acid is from about 2:1 to about 6:1.

When the level of $C_{12}-C_{18}$ mild surfactant is from about 20% to about 35%, the ratio of said stearic acid to said lauric acid is from about 0:1 to about 2:1.

The formulation of synthetic detergent-based (syndet) bars is a delicate balancing act. There are numerous bar use properties to take into consideration: lather, messiness, economy, product pH, bar firmness, etc.

The terms "synthetic bar," also "syndet bar," as used herein mean that the "bar" has more synthetic surfactant than soap unless otherwise specified. The term "AS syndet bar" means a syndet bar containing alkyl sulfate surfactant or its equivalent, unless otherwise specified. The term "long chain" means $C_{15}$ and $C_{22}$, preferably $C_{16}-C_{20}$, and mixtures thereof. The terms "$C_{12}-C_{18}$ acyl" and "cocoyl" as used herein are synonymous.

The percentages, ratios, and parts herein are on a total composition weight basis, unless otherwise specified. All levels and ranges herein are approximations, unless otherwise specified. Levels of ingredients are expressed herein on a "solids" basis, incorporating all non-water components together, unless otherwise specified.

A preferred surfactant system includes a long chain alkyl sulfate (hereinafter including its long chain equivalent synthetic surfactants). It is defined herein, as comprising $C_{16}-C_{18}$ alkyl chains at a level of at least about 90%, preferably about 93%, and more preferably about 97%. The long chain alkyl sulfate (and its equivalents) is derived from corresponding saturated straight chain alcohols. The preferred alkyl sulfate has a ratio of $C_{16}-C_{18}$ alkyl chains in the range of from about 100% $C_{16}$ to about 100% $C_{18}$ by weight. A commercially available $C_{16}-C_{18}$ alkyl sulfate is SIPON® EC-111 (formerly SIPEX® EC-111), sodium cetearyl sulfate, which is approximately 60% $C_{16}$ and 36% $C_{18}$. SIPON® EC-111 is sold by Alcolac Company, Baltimore, MD 21226. Another source is Henkel Corp., Ambler, Pa. 19002. Henkel's sodium cetearyl sulfate, LANETTE E, is an estimated 50-50% $C_{16}-C_{18}$ active alkyl sulfate sold as an emulsifier.

Other long chain surfactants which are equivalents to the long chain alkyl sulfate (mostly insoluble) could serve as either full or partial replacements for the long chain alkyl sulfate. Examples include long chain isethionates, sarcosinates, glyceryl ether sulfonates, etc., which have the same low solubility. The acyl esters of isethionic acid salts, with high levels of esters of $C_{16}-C_{18}$ acyl isethionates and no more than 25% or lower $C_{14}$ acyl groups are also useful. Preferred is stearoyl isethionate with $C_{14}$ 3%; $C_{16}$ 50%; and $C_{18}$ 47%. Some preferred compositions include from about 3% to about 20% of stearayl isethionate.

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radiolabeled water ($^3H-H_2O$) which passes from the test solution through the skin epidermis into the physiological buffer contained in the diffusate chamber. This test is described by T. J. Franz in the J. Invest. Dermatol., 1975, 64, pp. 190-195; and in U.S. Pat. No. 4,673,525, Small et al., issued Jun. 16, 1987, incorporated herein by reference, and which disclose a mild alkyl glyceryl ether sulfonate (AGS) surfactant based synbar comprising a "standard" alkyl glyceryl ether sulfonate mixture. Barrier destruction testing surprisingly shows that the long chain alkyl sulfates are milder than standard AGS. The long chain surfactants and especially long chain alkyl sulfate preferably comprise 5%-25% by weight of the bars of this invention.

The present invention contains a mild lathering surfactant at a level of from about 20% to about 70%, preferably from about 30% to about 60%. Examples of a high lathering or lather enhancing surfactant, especially milder ones, are: acyl isethionates; sodium acyl sarcosinate, and alkyl glyceryl ether sulfonate, especially those containing $C_{12}-C_{14}$ alkyl/acyl groups.

The isethionates, sarcosinates, and glyceryl ether sulfonates may be pure chain length variants or those derived from commercial oils such as coconut oil. The lauryl chain length should preferably account for at least 20% to as much as 100% of the weight of the given mild surfactant.

A "high lathering surfactant" as defined herein, is one which lathers better than the long chain $C_{16}-C_{18}$ alkyl sulfate.

A "mild surfactant" as defined herein is one that is milder than sodium dodecyl sulfate.

Numerous examples of surfactants in general are disclosed in the patents incorporated herein by reference. They include limited amounts of anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these other surfactants are $C_8-C_{22}$, preferably $C_{10}-C_{18}$. Alkyl glycosides and methyl glucoside esters are preferred mild nonionics which may be mixed with other mild anionic or amphoteric surfactants in the compositions of this invention.

The bars of this invention can have up to about 10% of high lathering, non-mild surfactants and still maintain the mildness requirement of the bar. Examples of these surfactants include linear alkyl benzene sulfonates and shorter chain or traditional (coconut) alkyl sulfates.

A preferred syndet bar contains a mixture of $C_{12}-C_{18}$ acyl isethionate (SCI) and sodium linear alkylbenzene sulfonate in a ratio of from about 35:1 to about 15:1, preferably from about 30:1 to about 20:1.

The primary plastic binders of the present invention are: (1) free fatty acid and (2) paraffin wax.

The fatty acid material which is desirably incorporated into the present invention includes material ranging in hydrocarbon chain length of from about 10 to about 22, essentially saturated. These fatty acids can be highly purified individual chain lengths and/or crude mixtures such as those derived from fats and oils.

The preferred ratio of stearic to lauric acids is dependent upon the level of mild synthetic surfactant(s), e.g., $C_{12}-C_{14}$ acyl isethionate, in the bar. Products that have higher levels of acyl isethionate require a larger ratio of stearic to lauric acid. The ratio is critical to the overall acceptability of a given product since it impacts product lather and smear as well as processability. For high levels of acyl isethionate (>40%), the preferred ratio of stearic:lauric is from about 5:1 to about 10:1, more preferably from about 6:1 to about 9:1; for moderate levels of acyl isethionate (between 45% and 30%), the preferred ratio of stearic:lauric is from about 2:1 to about 6:1, more preferably from about 3:1 to about 5:1; for low levels of acyl isethionate (<35%), the preferred ratio of stearic:lauric is from all lauric to about 2:1, more preferably from all lauric to about 0.5:1.

The composition may include soaps derived from hydrocarbon chain lengths of from about 10 to about 22 (including carboxyl carbon) and are preferably saturated. It is preferred that the soap be the sodium salt, but other soluble soap can be used. Potassium, ammonium, triethanolammonium, and mixtures thereof, are deemed acceptable. The soaps are preferably prepared by the in situ saponification of the corresponding fatty acids, but they may also be introduced as preformed soaps. Either some or all of the soap is preferably precomplexed with cationic polymer, or polymers, as described below.

"Insoluble" soaps, e.g., magnesium and zinc soaps, are not included in the 2%-15% level of "soap" in the composition definition. However, insoluble soaps can be used as non-lathering, non-soil-load diluents.

A highly preferred component of this invention is a paraffin wax having a melting point (M.P.) of from about 130° F. to about 180° F. (54°-82° C.), preferably from about 140° F. to about 165° F. (60°-74° C.), and most preferably from about 142° F. to about 160° F. (61°-71° C.). A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975.

The paraffin wax preferably is present in the bar in an amount ranging from about 4% to about 30% by weight. The paraffin wax ingredient is used in the product to impart skin mildness, plasticity, firmness, and processability. It also provides a glossy look and smooth feel to the bar.

The paraffin ingredient is optionally supplemented by a microcrystalline wax. A suitable microcrystalline wax has a melting point ranging, for example, from about 140° F. (60° C.) to about 185° F. (85° C.), preferably from about 145° F. (62° C.) to about 175° F. (79° C.) The wax preferably should meet the FDA requirements for food grade microcrystalline waxes. A very suitable microcrystalline wax is obtained from Witco Chemical Company under the trade name Multiwax X-145A. The microcrystalline wax preferably is present in the bar in an amount ranging from about 0.5% to about 5% by weight. The microcrystalline wax ingredient imparts pliability to the bar at room temperatures.

Auxiliary plastic binders can be incorporated into the bar at levels of from 0% to about 10%. These binders can be selected from monoglycerides, polyethylene glycols, fatty alcohols, sugars, tallow alcohol ethoxylates, and mixtures thereof. Other plastic binders are identified in the published literature, such as J. Amer. Oil Chem. Soc. 1982, 59, 442. The binder system can contain several plasticizers.

The syndet bar of this invention may comprise from 0% to about 5%, preferably from about 0.3% to about 4%, of a suitably fast hydrating cationic polymer. The polymers have molecular weights of from about 1,000 to about 5,000,000.

The cationic polymer (skin conditioning agent) is selected, e.g., from the group consisting of:
(I) cationic polysaccharides;
(II) cationic copolymers of saccharides and synthetic cationic monomers, and
(III) synthetic polymers selected from the group consisting of:
  (A) cationic polyalkylene imines;
  (B) cationic ethoxy polyalkylene imines; and
  (C) cationic poly[N-[-3-(dimethylammonio)propyl]-N'-[3-(ethyleneoxyethylene dimethylammonio)propyl]urea dichloride].

Other ingredients of the present invention are selected for the various applications. E.g., perfumes can be used in formulating the skin cleansing products, generally at a level of from about 0.1% to about 1.5% of the composition. Alcohols, hydrotropes, colorants, and fillers such as talc, clay, calcium carbonate and dextrin can also be used. Cetearyl alcohol is a mixture of cetyl and stearyl alcohols. Preservatives, e.g., trisodium etidronate and sodium ethylenediaminetetraacetate (EDTA), generally at a level of less than 1% of the composition, can be incorporated in the cleansing products to prevent color and odor degradation. Antibacterials can also be incorporated, usually at levels up to 1.5%. Salts, both organic and inorganic, can be incorporated. Examples include sodium chloride, sodium isethionate, sodium sulfate, and their equivalents. The following patents disclose or refer to such ingredients and formulations which can be used in the soap/synbars of this invention, and are incorporated herein by reference:

| U.S. Pat. No. | Issue Date | Inventor(s) |
|---|---|---|
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,673,525 | 6/1987 | Small et al. |
| 4,704,224 | 11/1987 | Saud |
| 4,812,253 | 3/1989 | Small et al. |
| 4,820,447 | 4/1989 | Medcalf et al. |
| 4,954,282 | 9/1990 | Rys et al. |

The syndet bars of this invention have a pH of from 4 to 9 in a 1% aqueous solution. The preferred pH is from about 5 to about 8, more preferably about 6.5 to about 7.5.

A Method of Making Zeolite Containing Syndet Bars

Crutching (Alternative Procedures)

A

1. Add melted cetearyl sulfate (50°-75° C.); begin agitation
2. Add NaCl, then TiO$_2$, then EDTA, then etidronate, and bring crutcher mixture to −77° C. under low agitation.
3. Add the preweighed sodium linear alkyl benzene sulfonate. Mix for 5-10 minutes.
4. Add premeasured caustic and continue to mix slowly.
5. Steam sparge to 77°-80° C. before adding remaining ingredients.
6. Add stearic acid and mix for 5-10 minutes at −77°-80° C.
7. Add the final molten premix of paraffin/SCI/SI/FA and continue mixing slowly for approximately 15-30 minutes while maintaining the mix temperature at 70°-80° C.
8. Sprinkle in the deodorizing powder and allow to disperse through the mixture thoroughly for approximately 15 minutes.

B

1. Add the molten premix of paraffin/SCI/SI/FA and begin agitating slowly while maintaining the temperature at 70°-80° C.
2. Add molten cetearyl sulfate (50°-75° C.) and maintain slow agitation and recirculation.
3. Add NaCl, then TiO$_2$ then EDTA, then etidronate, and continue to maintain the temperature in the 50°-70° C. range under low agitation and continual recirculation.
4. Next add the preweighed sodium linear alkyl benzene sulfonate. Continue to agitate and recirculate.
5. Add the premeasured caustic and continue to mix slowly.
6. Add the remaining required stearic acid and mix for another 10 minutes at the higher end of the temperature range of 50°-75° C. Check for uniform consistency of the crutcher batch.
7. Sprinkle in the deodorizing powder and allow to disperse thoroughly before pumping the mixture to the hold tank.

C

1. Add molten cetearyl sulfate (50°-75° C.) to the crutcher and begin slow agitation.
2. Add the molten premix of paraffin/SCI/SI/FA and continue to mix with agitation and begin recirculation.
3. Add NaCl, then TiO$_2$, then EDTA, then etidronate, and continue to maintain the temperature in the 50°-70° C. temperature range while agitating and recirculating.
4. Next add the preweighed sodium linear alkyl benzene sulfonate. Continue to agitate and recirculate.
5. Add the premeasured caustic and continue to mix slowly.
6. Add the remaining required stearic acid and mix for another 10 minutes at the higher end of the temperature range of 50°-75° C. Check for uniform consistency of the crutcher batch and continue to m x until fluid and lump free.
7. Sprinkle in the deodorizing powder and allow to disperse thoroughly before pumping the mixture to the hold tank.

Drying

The crutcher mix is dried and cooled using a combination flash chamber and chill roll or chill belt. The crutcher mix is first heated to approximately 265°-275° F. (130°-1235° C.) by a heat exchanger and then flash dried in a chamber above the chill roll or chill belt. The chill belt or chill roll provides a uniform, thin cool (85°-95° F.; 29°-35° C.) product in flake or chip form. Typical moisture for the flake is from about 1% to about 10%, preferably from about 3% to about 5.5-6.5% ±1. The way to regu-late the moisture, in the order of preference, are: (1) increasing or decreasing steam pressure on the heat exchanger; (2) increasing or decreasing crutcher mix rate to the heat exchanger; and (3) increasing or decreasing crutcher mix temperature to the heat exchanger.

Amalgamating

The flakes are weighed and added to a batch amalgamator to obtain uniform flake size and a course mixture of additives that may be brought into the flake mixture (syndet or soap).

Alternative Procedures

A. Preweighed flakes may be amalgamated to uniform size and a premeasured amount of zeolite deodorizing powder sprinkled into the base flakes and mixed for several minutes with no perfume being added.
B. Preweighed flakes may be amalgamated to uniform size and a premeasured amount of deodorizing powder sprinkled into the base flakes and admixed for several minutes before; then adding a premeasured amount of perfume. Continue amalgamating for at lease one minute to thoroughly mix together the ingredients.

Milling

The 3-roll soap mills are set up with the first roll at −120° F. (49° C.), the second roll at −100° F. (38° C.), and the final roll at −68° F. (20° C.). The material is passed through the mills several times to provide a homogeneous mixture of perfume and dried flakes.

Plodding and Stamping

The plodder is set up with the barrel temperature at about 115° F. (46° C.) and the nose temperature at 114°–122° F. (45°–50° C.). The ideal plodder is a dual stage plodder that allows use of a vacuum of about 15-25 inches (38-64 cm) of Hg. The plugs should be cut in 5 inch (13 cm) sections and stamped with a cold die block using die liquor such as alcohol, if appropriate.

Laboratory Assessment of Bar

The following test procedures are used to evaluate the critical bar performance attributes of malodor and bar feel.

Odor Evaluation

Samples to be graded are placed in clean 12 oz. paper cups with corresponding lids. A standard bar of the same composition as the sample is placed in a similar cup. Bars are aged at least 24 hours before grading.

The order of grading multiple bar soap versions is as follows: unscented standards and samples first; low perfume impact bar standards and samples next; higher perfume impact bars last. The procedure of evaluation is to compare the sample product against a standard quality bar of known quality and grade. Differences in perfume impact, character and base notes are evaluated with each test. Unscented bars are compared to a standard of "good" quality and grades given are good, fair or poor, by trained observers. Scented products are graded on a scale of 1–10 with the standard quality bar a grade of 9.0. Wet grades are evaluated with the same appropriate scale as the neat grades. A wet grade is performed by washing with the bar, paying close attention to the lather odor and the bar odor itself.

Bar Feel

A standard washing procedure in 26° C. (80° F.) water is followed by estimation of grittiness by feel, a trained observer. Grades have been represented here on a good, sandy scale where sandy is unacceptable.

Examples and Formulas

The following examples and formulas are illustrative and are not intended to limit the scope of the invention. The methods of making milled bars are well known. All labels and ranges, temperatures, results, etc., used herein are approximations unless otherwise specified. Therefore, the percentages do not necessarily add up to 100%.

The level of the water in the above syndet bars stabilizes upon storage, at from about 6% to about 3%.

The base formula for the Examples is shown below in Table 1. Table 2 lists additions made for each Example (if any) and odor and bar feel performance.

Comparative Examples A and B are about the same as the Base Formula.

TABLE 1

| Base Formula Without Zeolite | |
|---|---|
| Ingredient | Wt. % |
| Sodium Cocoyl Isethionate | 49.00 |
| Sodium Linear Alkyl Benzene Sulfonate | 2.00 |
| Sodium Cetearyl Sulfate | 11.40 |
| Paraffin | 9.80 |
| Sodium Soap (in situ) | 4.60 |

TABLE 1-continued

| Base Formula Without Zeolite | |
|---|---|
| Ingredient | Wt. % |
| Coconut Acid | 3.60 |
| Stearic Acid | 8.20 |
| Sodium Chloride | 0.50 |
| Sodium Isethionate | 5.90 |
| Titanium Dioxide | 0.40 |
| Perfume | 1.20 |
| Water | 4.60 |

TABLE 2

Bar Formula with Zeolite with Odor and Bar Feel Performance

| | A Wt. % | 1 Wt. % | B Wt. % | 2 Wt. % | 3 Wt. % | 4 Wt. % |
|---|---|---|---|---|---|---|
| Zeolite 1 | — | 0.50 | — | — | 0.75 | — |
| Zeolite 2 | — | — | — | 0.75 | — | — |
| Zeolite 3 | — | — | — | — | — | 1.0 |
| Odor | Fair | Good | Fair | Good | Good | Fair |
| Bar Feel | Good | Good | Good | Sandy* | Good | Good |

*Unacceptable
Zeolite 1 is VALFOR CP300-51.
Zeolite 2 is ABSCENTS.
Zeolite 3 is Georgia Kaolin.

EXAMPLES A-1

Comparative Example A and Example 1 demonstrate that an odor benefit is obtained with the addition of zeolite (VALFOR CP300-51 ®) to synthetic based bars. Comparative Example A contains no zeolite; it has a "fair" but unacceptable odor for a commercial personal cleansing bar. Example 1 demonstrates that when zeolite is incorporated into the synthetic-based bar the base odor is significantly reduced; it is acceptable, "good."

EXAMPLES 2-3 AND COMPARATIVE B

Examples 2, 3 and Comparative B demonstrate the importance of particle size on bar feel. Example 2, containing ABSCENTS (UOP) demonstrates that when the zeolite has too many larger (6.5%) particles above 15 microns, bar feel decreases significantly. The zeolite ABSCENTS has more particles sized over 15 microns than VALFOR CP300-51 ® zeolite sample which is analyzed to have about 2.5% particles over 15 microns. Example 3 with VALFOR CP300-51 has no significant effect on bar feel versus the Base Formula without zeolite Comparative Example B.

EXAMPLE 4

Example 4 demonstrates that an odor-containing benefit is not obtained by using a hydrophilic clay. The clay used in this Example is Georgia Kaolin clay.

TABLE 3

| All Soap Bar Formula | | |
|---|---|---|
| | Comparative Example: | |
| Ingredient | 5 Wt. % | 6 Wt. % |
| Tallow Soap | 30 | 30 |
| Palm Oil Stearate Soap | 30 | 30 |
| Palm Kernel Oil Soap | 40 | 40 |
| VALFOR CP300-51 | 0 | 1 |
| Odor | Fair | Fair |

COMPARATIVE EXAMPLES 5-6

Comparative Example 5 vs. Comparative Example 6 demonstrates that selectivity is required in selecting the odor adsorbing zeolite for a particular matrix. VALFOR CP300-51 is added to an all soap bar formula, Comp. Example 5, and compared to the same base formula soap bar with VALFOR CP300-51, Comp. Example 6. Surprisingly, no odor benefit is obtained by the addition of this zeolite.

EXAMPLE 7

VALFOR CP300-51 is added to the following perfume-free formula for improved malodor reduction.

TABLE 4

Unscented Base Formula D

| Ingredient | Wt. % |
| --- | --- |
| Sodium Cocoyl Isethionate | 45.25 |
| Sodium Isethionate | 2.60 |
| Sodium Dodecylbenzene Sulfonate | 1.80 |
| Stearic Acid | 26.00 |
| Sodium Soap | 11.70 |
| Sodium Chloride | 0.35 |
| Titanium Dioxide | 0.40 |
| Coconut Fatty Acid | 2.50 |
| Sodium Stearate | 2.40 |
| Water | 7.00 |
| Miscellaneous | 0.25 |

What is claimed is:

1. A personal cleansing bar composition essentially free of raw material malodors comprising:
   A. an odor-controlling amount of intermediate ratio $(SiO_2:Al_2O_3)Y$ zeolite;
   B. from about 4% to about 32% of essentially saturated long chain ($C_{15}$–$C_{22}$ alkyl) synthetic surfactant selected from the group consisting of: alkyl sulfate, acyl isethionate, alkyl sarcosinate, alkyl glyceryl ether sulfonate, and mixtures thereof;
   C. from about 4% to about 30% of paraffin wax having a melting point of from about 130° F./54° C. to about 180° F./82° C.;
   D. from about 20% to about 70% lathering mild synthetic surfactant; and wherein said lathering mild synthetic surfactant is selected from $C_{12}$–$C_{18}$ acyl isethionate, $C_{12}$–$C_{14}$ alkyl glyceryl ether sulfonate, $C_{12}$–$C_{18}$ acyl sarcosinate, and mixtures thereof and wherein at least about 10% of said bar is said mild lathering $C_{12}$–$C_{18}$ acyl isethionate;
   E. from about 2% to about 30% free fatty acid;
   F. from 0% to about 15% soap;
   G. from about 2% to about 8% sodium isethionate;
   H. from 0% to about 2% sodium chloride;
   I. from about 1.5% to about 10% water; and
   J. from 0% to about 5% of a polymer.

2. A personal cleansing bar composition according to claim 1 wherein the zeolite's $(SiO_2:Al_2O_3)Y$ molar ratio is from about 2:1 to about 50:1, said zeolite being in the protonic, sodium, potassium, ammonium, or alkylammonium form and said soap level is from about 2% to about 10%.

3. A personal cleansing bar composition according to claim 2 wherein the zeolite's $(SiO_2:Al_2O_3)Y$ molar ratio is from about 2:1 to about 20:1, said zeolite being in the protonic, sodium, potassium, ammonium, or alkylammonium form.

4. A personal cleansing bar composition according to claim 3 wherein the zeolite's $(SiO_2:Al_2O_3)Y$ molar ratio is from about 2:1 to about 10:1, said zeolite being in the protonic, sodium, potassium, ammonium, or alkylammonium form.

5. A personal cleansing bar composition according to claim 4 wherein the zeolite is at a level of from about 0.05% to about 5% by weight of the composition.

6. A personal cleansing bar composition according to claim 5 wherein the zeolite is in the protonic sodium form.

7. A personal cleansing bar composition according to claim 1 wherein the bar contains from about 0.5% to about 5% of microcrystalline wax.

8. A personal cleansing bar composition according to claim 1 wherein the polymer is selected from the group consisting of: cationic polymer, anionic polymer, zwitterionic polymer, and mixtures, thereof.

9. A personal cleansing bar composition according to claim 1 wherein the zeolite is at a level of from about 0.05% to about 5% by weight of the composition.

10. A personal cleansing bar composition according to claim 1 wherein the zeolite's $(SiO_2:Al_2O_3)Y$ molar ratio is from about 2:1 to about 50:1, said zeolite being in the protonic, sodium potassium, ammonium, or alkylammonium form, and said composition contains no perfume.

11. A personal cleansing bar composition according to claim 1 wherein the zeolite's $(SiO_2:Al_2O_3)Y$ molar ratio is from about 2:1 to about 20:1, said zeolite being in the protonic, sodium, potassium, ammonium, or alkylammonium form; and wherein said bar composition contains perfume.

12. A personal cleansing bar comprising an effective amount of a malodor absorbing zeolite and:
   A. from about 4% to about 32% of essentially saturated long chain ($C_{15}$–$C_{22}$) synthetic surfactant selected from the group consisting of: alkyl sulfate, acyl isethionate, alkyl sarcosinate, alkyl glyceryl ether sulfonate, and mixtures thereof;
   B. from about 4% to about 30% of paraffin wax having a melting point of from about 130° F./54° C. to about 180° F./82° C.;
   C. from about 20% to about 35% lathering mild synthetic surfactant selected from $C_{12}$–$C_{18}$ acyl isethionate, $C_{12}$–$C_{14}$ alkyl glyceryl ether sulfonate, $C_{12}$–$C_{18}$ sodium acyl sarcosinate, and mixtures thereof; and wherein at least about 10% of said bar is said mild lathering $C_{12}$–$C_{18}$ acyl isethionate;
   D. from about 2% to about 30% free fatty acid; wherein said fatty acid is selected from the group consisting of stearic and lauric acids; wherein the ratio of said stearic acid to said lauric acid is from about 0:1 to about 2:1, and mixtures thereof;
   E. from about 2% to about 15% soap;
   F. from about 2% to about 8% sodium isethionate;
   G. from 0% to about 2% sodium chloride;
   H. from about 1.5% to about 10% water;
   I. from 0% to about 5% of cationic polymer;
   J. from 0% to about 2% perfume; and
wherein said bar has a pH of from about 4.0 to about 9.0.

* * * * *